US009114198B2

(12) United States Patent
Hossainy et al.

(10) Patent No.: US 9,114,198 B2
(45) Date of Patent: *Aug. 25, 2015

(54) BIOLOGICALLY BENEFICIAL COATINGS FOR IMPLANTABLE DEVICES CONTAINING FLUORINATED POLYMERS AND METHODS FOR FABRICATING THE SAME

(75) Inventors: Syed F. A. Hossainy, Fremont, CA (US); Yiwen Tang, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2597 days.

This patent is subject to a terminal disclaimer.

(21) Appl. No.: 10/718,278

(22) Filed: Nov. 19, 2003

(65) Prior Publication Data

US 2005/0106204 A1    May 19, 2005

(51) Int. Cl.
| | | |
|---|---|---|
| *A61K 31/16* | (2006.01) | |
| *A61L 27/14* | (2006.01) | |
| *A61F 2/06* | (2006.01) | |
| *A61L 31/10* | (2006.01) | |

(52) U.S. Cl.
CPC .................................... *A61L 31/10* (2013.01)

(58) Field of Classification Search
CPC ....... A61L 31/04; A61L 31/041; A61L 31/16; A61L 29/08; A61L 29/085; A61L 29/12; A61L 29/16; C08L 27/12; C08L 71/02; C08L 101/04; C08L 67/02
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 3,178,399 A | 4/1965 | Lo | |
| 3,773,737 A | 11/1973 | Goodman et al. | |
| 3,849,514 A | 11/1974 | Gray, Jr. et al. | |
| 4,226,243 A | 10/1980 | Shalaby et al. | |
| 4,304,767 A | 12/1981 | Heller et al. | |
| 4,329,383 A | 5/1982 | Joh | 428/36 |
| 4,343,931 A | 8/1982 | Barrows | |
| 4,368,090 A | 1/1983 | Mumcu et al. | |
| 4,483,975 A | 11/1984 | De Jong et al. | |
| 4,529,792 A | 7/1985 | Barrows | |
| 4,564,013 A | 1/1986 | Lilenfeld et al. | |
| 4,611,051 A | 9/1986 | Hayes et al. | |
| 4,656,242 A | 4/1987 | Swan et al. | |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

Webster's Collegiate Dictionary . 1981, p. 14.*

(Continued)

*Primary Examiner* — Lakshmi Channavajjala
(74) *Attorney, Agent, or Firm* — Squire Patton Boggs (US) LLP (57) ABSTRACT

Coatings for an implantable medical device and a method of fabricating the coatings are disclosed. The coatings comprise a fluorinated polymer and a biologically beneficial polymer, an example of which includes poly(ethylene-glycol)-block poly(butylene terephthalate)-block poly(ethylene-glycol). A biologically active agent can be additionally conjugated to the biologically beneficial polymer.

14 Claims, 2 Drawing Sheets

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,816,339 A | 3/1989 | Tu et al. | |
| 4,882,168 A | 11/1989 | Casey et al. | 424/468 |
| 4,886,062 A | 12/1989 | Wiktor | 128/343 |
| 4,910,276 A * | 3/1990 | Nakamura et al. | 526/247 |
| 4,931,287 A | 6/1990 | Bae et al. | |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | |
| 5,100,992 A | 3/1992 | Cohn et al. | |
| 5,112,457 A | 5/1992 | Marchant | 204/165 |
| 5,133,742 A | 7/1992 | Pinchuk | |
| 5,163,952 A | 11/1992 | Froix | |
| 5,165,919 A | 11/1992 | Sasaki et al. | 424/488 |
| 5,219,980 A | 6/1993 | Swidler | |
| 5,258,020 A | 11/1993 | Froix | |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,485,496 A | 1/1996 | Lee et al. | |
| 5,489,667 A | 2/1996 | Knipf et al. | |
| 5,509,899 A | 4/1996 | Fan et al. | |
| 5,516,781 A | 5/1996 | Morris et al. | |
| 5,516,881 A | 5/1996 | Lee et al. | |
| 5,563,146 A | 10/1996 | Morris et al. | |
| 5,569,463 A | 10/1996 | Helmus et al. | 424/426 |
| 5,578,073 A | 11/1996 | Haimovich et al. | 623/1 |
| 5,581,387 A | 12/1996 | Cahill | |
| 5,584,877 A | 12/1996 | Miyake et al. | |
| 5,603,894 A | 2/1997 | Aikus et al. | |
| 5,605,696 A | 2/1997 | Eury et al. | 424/423 |
| 5,607,467 A | 3/1997 | Froix | |
| 5,609,629 A | 3/1997 | Fearnot et al. | 623/1 |
| 5,610,241 A | 3/1997 | Lee et al. | |
| 5,616,338 A | 4/1997 | Fox, Jr. et al. | |
| 5,624,411 A | 4/1997 | Tuch | 604/265 |
| 5,628,730 A | 5/1997 | Shapland et al. | 604/21 |
| 5,644,020 A | 7/1997 | Timmermann et al. | |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,708,044 A * | 1/1998 | Branca | 521/145 |
| 5,711,958 A | 1/1998 | Cohn et al. | |
| 5,716,981 A | 2/1998 | Hunter et al. | 514/449 |
| 5,721,131 A | 2/1998 | Rudolph et al. | |
| 5,723,219 A | 3/1998 | Kolluri et al. | |
| 5,735,897 A | 4/1998 | Buirge | 623/12 |
| 5,746,998 A | 5/1998 | Torchilin et al. | 424/9.4 |
| 5,759,205 A | 6/1998 | Valentini | |
| 5,776,184 A | 7/1998 | Tuch | 623/1 |
| 5,783,657 A | 7/1998 | Pavlin et al. | |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | |
| 5,849,859 A | 12/1998 | Acemoglu | |
| 5,851,508 A | 12/1998 | Greff et al. | 424/9.411 |
| 5,854,376 A | 12/1998 | Higashi | |
| 5,858,746 A | 1/1999 | Hubbell et al. | 435/177 |
| 5,861,387 A | 1/1999 | Labrie et al. | |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | |
| 5,880,220 A | 3/1999 | Warzelhan et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | 525/523 |
| 5,932,299 A | 8/1999 | Katoot | |
| 5,955,509 A | 9/1999 | Webber et al. | 514/772.7 |
| 5,958,385 A | 9/1999 | Tondeur et al. | |
| 5,962,138 A | 10/1999 | Kolluri et al. | |
| 5,962,516 A | 10/1999 | Qi et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,491 A | 9/2000 | Kohn et al. | |
| 6,120,536 A | 9/2000 | Ding et al. | 623/1.43 |
| 6,120,788 A | 9/2000 | Barrows | |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | |
| 6,143,354 A | 11/2000 | Koulik et al. | |
| 6,153,252 A | 11/2000 | Hossainy et al. | 427/2.3 |
| 6,159,978 A | 12/2000 | Myers et al. | |
| 6,165,212 A | 12/2000 | Dereume et al. | 623/1.13 |
| 6,165,509 A * | 12/2000 | Hoffman et al. | 424/487 |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | 606/108 |
| 6,211,249 B1 | 4/2001 | Cohn et al. | |
| 6,214,901 B1 | 4/2001 | Chudzik et al. | |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | |
| 6,248,129 B1 | 6/2001 | Froix | |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | |
| 6,262,034 B1 | 7/2001 | Mathiowitz et al. | |
| 6,270,779 B1 * | 8/2001 | Fitzhugh et al. | 424/423 |
| 6,270,788 B1 | 8/2001 | Koulik et al. | |
| 6,273,913 B1 | 8/2001 | Wright et al. | |
| 6,277,449 B1 | 8/2001 | Kolluri et al. | |
| 6,277,927 B1 | 8/2001 | Roby et al. | |

(56) References Cited

U.S. PATENT DOCUMENTS

| | | | |
|---|---|---|---|
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,316,585 B1 | 11/2001 | Lele et al. | |
| 6,328,970 B1 * | 12/2001 | Molnar-Kimber et al. | 424/184.1 |
| 6,331,313 B1 | 12/2001 | Wong et al. | 424/427 |
| 6,331,547 B1 * | 12/2001 | Zhu et al. | 514/291 |
| 6,335,029 B1 | 1/2002 | Kamath et al. | |
| 6,344,035 B1 | 2/2002 | Chudzik et al. | |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,384,046 B1 | 5/2002 | Schuler et al. | |
| 6,387,379 B1 | 5/2002 | Goldberg et al. | |
| 6,395,326 B1 | 5/2002 | Castro et al. | 427/2.24 |
| 6,416,834 B1 * | 7/2002 | Fuller | 428/35.7 |
| 6,419,692 B1 | 7/2002 | Yang et al. | 623/1.15 |
| 6,420,045 B1 | 7/2002 | Faulhammer et al. | |
| 6,451,337 B1 * | 9/2002 | Smith et al. | 424/445 |
| 6,451,373 B1 | 9/2002 | Hossainy et al. | 427/2.25 |
| 6,482,834 B2 | 11/2002 | Spada et al. | |
| 6,494,862 B1 | 12/2002 | Ray et al. | 604/96.01 |
| 6,503,538 B1 | 1/2003 | Chu et al. | |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,517,858 B1 | 2/2003 | Haberbosch et al. | |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Hossaony et al. | |
| 6,623,448 B2 | 9/2003 | Slater | |
| 6,625,486 B2 | 9/2003 | Lundkvist et al. | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |
| 6,673,385 B1 | 1/2004 | Ding et al. | |
| 6,689,099 B2 | 2/2004 | Mirzaee | |
| 6,695,920 B1 | 2/2004 | Pacetti et al. | |
| 6,703,040 B2 * | 3/2004 | Katsarava et al. | 424/444 |
| 6,706,013 B1 | 3/2004 | Bhat et al. | |
| 6,709,514 B1 | 3/2004 | Hossainy | |
| 6,712,845 B2 | 3/2004 | Hossainy | |
| 6,713,119 B2 | 3/2004 | Hossainy et al. | |
| 6,716,444 B1 | 4/2004 | Castro et al. | |
| 6,723,120 B2 | 4/2004 | Yan | |
| 6,733,768 B2 | 5/2004 | Hossainy et al. | |
| 6,740,040 B1 | 5/2004 | Mandrusov et al. | |
| 6,743,462 B1 | 6/2004 | Pacetti | |
| 6,749,626 B1 | 6/2004 | Bhat et al. | |
| 6,753,071 B1 | 6/2004 | Pacetti et al. | |
| 6,756,458 B2 * | 6/2004 | Kashiwagi et al. | 526/252 |
| 6,758,859 B1 | 7/2004 | Dang et al. | |
| 6,759,054 B2 | 7/2004 | Chen et al. | |
| 6,759,129 B2 * | 7/2004 | Fukushi | 428/412 |
| 6,764,505 B1 | 7/2004 | Hossainy et al. | |
| 6,953,560 B1 * | 10/2005 | Castro et al. | 423/423 |
| 7,011,812 B1 * | 3/2006 | Griffiths et al. | 424/1.49 |
| 7,056,550 B2 * | 6/2006 | Davila et al. | 427/2.24 |
| 7,063,884 B2 | 6/2006 | Hossainy et al. | |
| 7,169,404 B2 * | 1/2007 | Hossainy et al. | 424/423 |
| 7,345,053 B2 * | 3/2008 | Garvey | 514/291 |
| 7,731,987 B2 | 6/2010 | DesNoyer et al. | |
| 2001/0007083 A1 | 7/2001 | Roorda | |
| 2001/0014717 A1 | 8/2001 | Hossainy et al. | |
| 2001/0018469 A1 | 8/2001 | Chen et al. | 523/121 |
| 2001/0020011 A1 | 9/2001 | Mathiowitz et al. | |
| 2001/0029351 A1 | 10/2001 | Falotico et al. | |
| 2001/0037145 A1 | 11/2001 | Guruwaiya et al. | 623/1.15 |
| 2001/0051608 A1 | 12/2001 | Mathiowitz et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0009604 A1 | 1/2002 | Zamora et al. | |
| 2002/0016625 A1 | 2/2002 | Falotico et al. | |
| 2002/0032213 A1 | 3/2002 | Navarro et al. | |
| 2002/0032414 A1 | 3/2002 | Ragheb et al. | |
| 2002/0032434 A1 | 3/2002 | Chudzik et al. | |
| 2002/0051730 A1 | 5/2002 | Bodnar et al. | |
| 2002/0071822 A1 | 6/2002 | Uhrich | |
| 2002/0077693 A1 | 6/2002 | Barclay et al. | 623/1.13 |
| 2002/0082679 A1 | 6/2002 | Sirhan et al. | |
| 2002/0087123 A1 | 7/2002 | Hossainy et al. | |
| 2002/0091230 A1 | 7/2002 | Mao et al. | |
| 2002/0091433 A1 | 7/2002 | Ding et al. | 623/1.2 |
| 2002/0094440 A1 | 7/2002 | Llanos et al. | |
| 2002/0111590 A1 | 8/2002 | Davila et al. | |
| 2002/0120326 A1 | 8/2002 | Michal | |
| 2002/0123801 A1 | 9/2002 | Pacetti et al. | |
| 2002/0142039 A1 | 10/2002 | Claude | |
| 2002/0155212 A1 | 10/2002 | Hossainy | 427/2.25 |
| 2002/0165608 A1 | 11/2002 | Llanos et al. | |
| 2002/0176849 A1 | 11/2002 | Slepian | |
| 2002/0183581 A1 | 12/2002 | Yoe et al. | |
| 2002/0188037 A1 | 12/2002 | Chudzik et al. | |
| 2002/0188277 A1 | 12/2002 | Roorda et al. | |
| 2003/0004141 A1 | 1/2003 | Brown | |
| 2003/0028243 A1 | 2/2003 | Bates et al. | |
| 2003/0028244 A1 | 2/2003 | Bates et al. | |
| 2003/0031780 A1 | 2/2003 | Chudzik et al. | |
| 2003/0032767 A1 | 2/2003 | Tada et al. | |
| 2003/0036794 A1 | 2/2003 | Ragheb et al. | |
| 2003/0039689 A1 | 2/2003 | Chen et al. | |
| 2003/0040712 A1 | 2/2003 | Ray et al. | |
| 2003/0040790 A1 | 2/2003 | Furst | |
| 2003/0059520 A1 | 3/2003 | Chen et al. | |
| 2003/0060877 A1 | 3/2003 | Falotico et al. | |
| 2003/0065377 A1 | 4/2003 | Davila et al. | 623/1.13 |
| 2003/0072868 A1 | 4/2003 | Harish et al. | |
| 2003/0073961 A1 | 4/2003 | Happ | |
| 2003/0083646 A1 | 5/2003 | Sirhan et al. | |
| 2003/0083739 A1 | 5/2003 | Cafferata | |
| 2003/0097088 A1 | 5/2003 | Pacetti | |
| 2003/0097173 A1 | 5/2003 | Dutta | |
| 2003/0099712 A1 | 5/2003 | Jayaraman | 424/486 |
| 2003/0105518 A1 | 6/2003 | Dutta | |
| 2003/0113439 A1 | 6/2003 | Pacetti et al. | |
| 2003/0150380 A1 | 8/2003 | Yoe | |
| 2003/0157241 A1 | 8/2003 | Hossainy et al. | |
| 2003/0158517 A1 | 8/2003 | Kokish | |
| 2003/0190406 A1 | 10/2003 | Hossainy et al. | |
| 2003/0207020 A1 | 11/2003 | Villareal | |
| 2003/0211230 A1 | 11/2003 | Pacetti et al. | |
| 2004/0001889 A1 * | 1/2004 | Chen et al. | 424/468 |
| 2004/0018296 A1 | 1/2004 | Castro et al. | |
| 2004/0029952 A1 | 2/2004 | Chen et al. | |
| 2004/0034409 A1 | 2/2004 | Heublein et al. | |
| 2004/0047978 A1 | 3/2004 | Hossainy et al. | |

(56) References Cited

U.S. PATENT DOCUMENTS

| | | | |
|---|---|---|---|
| 2004/0047980 A1 | 3/2004 | Pacetti et al. | |
| 2004/0052858 A1 | 3/2004 | Wu et al. | |
| 2004/0052859 A1 | 3/2004 | Wu et al. | |
| 2004/0054104 A1 | 3/2004 | Pacetti | |
| 2004/0060508 A1 | 4/2004 | Pacetti et al. | |
| 2004/0062853 A1 | 4/2004 | Pacetti et al. | |
| 2004/0063805 A1 | 4/2004 | Pacetti et al. | |
| 2004/0071861 A1 | 4/2004 | Mandrusov et al. | |
| 2004/0072857 A1* | 4/2004 | Waugh et al. | 514/291 |
| 2004/0072922 A1 | 4/2004 | Hossainy et al. | |
| 2004/0073297 A1 | 4/2004 | Rohde et al. | |
| 2004/0073298 A1 | 4/2004 | Hossainy | |
| 2004/0086542 A1 | 5/2004 | Hossainy et al. | |
| 2004/0086550 A1 | 5/2004 | Roorda et al. | |
| 2004/0096504 A1 | 5/2004 | Michal | |
| 2004/0098110 A1 | 5/2004 | Williams et al. | |
| 2004/0098117 A1 | 5/2004 | Hossainy et al. | |
| 2004/0126405 A1 | 7/2004 | Sahatjian et al. | |
| 2004/0170685 A1* | 9/2004 | Carpenter et al. | 424/468 |
| 2004/0180039 A1 | 9/2004 | Toner et al. | |
| 2005/0008671 A1 | 1/2005 | Van Antwerp | |
| 2005/0084515 A1 | 4/2005 | Udipi et al. | |
| 2005/0137715 A1 | 6/2005 | Phan et al. | |
| 2005/0147643 A1* | 7/2005 | Hunter et al. | 424/423 |
| 2005/0147647 A1 | 7/2005 | Glauser et al. | |
| 2005/0233062 A1 | 10/2005 | Hossainy et al. | |
| 2005/0245637 A1 | 11/2005 | Hossainy et al. | |
| 2005/0265960 A1 | 12/2005 | Pacetti et al. | |
| 2005/0283229 A1 | 12/2005 | Dugan et al. | |
| 2007/0065480 A1* | 3/2007 | Claude | 424/423 |
| 2007/0098758 A1* | 5/2007 | Hossainy et al. | 424/423 |

FOREIGN PATENT DOCUMENTS

| | | |
|---|---|---|
| EP | 0 396 429 | 11/1990 |
| EP | 0 514 406 | 11/1992 |
| EP | 0 583 888 | 2/1994 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 778 250 | 6/1997 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0950386 A2 | 10/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| FR | 2 785 812 | 5/2000 |
| GB | 1 137 209 | 12/1968 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09010 | 4/1994 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/35575 | 10/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/32777 | 7/1998 |
| WO | WO 98/36784 | 8/1998 |
| WO | WO 98/38687 A1 | 9/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/56376 | 9/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/18477 | 3/2002 |
| WO | WO 02/26162 | 4/2002 |
| WO | WO 02/26281 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/014449 | 2/2004 |
| WO | WO 2004/022119 | 3/2004 |
| WO | WO 2004/101018 | 11/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/061024 | 7/2005 |
| WO | WO 2005/066241 | 7/2005 |

OTHER PUBLICATIONS

Wikipedia—Lysine (pp. 1-5).*
European Examination Report for EP 04 811 021, mailed Apr. 15, 2009, 2 pgs.
U.S. Appl. No. 10/630,250, filed Jul. 30, 2002, Pacetti et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Huang et al., *Biodegradable Polymers Derived from Aminoacids*, Macromol. Symp. 144, 7-32 (1999).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Moreno et al., *Macrophage Infiltration Predicts Restenosis Alter Coronary Intervention in Patients with Unstable Angina*, Circulation, vol. 94, No. 12, (1996) pp. 3098-3102.
Oikawa et al., Mechanisms of Acute Gain and Late Lumen Loss Alter Atherectomy in Different Preintervention Arterial Remodeling Patterns, *The Am. J. of Cardiology*, vol. 89, (2002) pp. 505-510.

(56) References Cited

OTHER PUBLICATIONS

Saotome, et al., *Novel Enzymatically Degradable Polymers Comprising α-Amino Acid, 1,2-Ethanediol, and Adipic Acid*, Chemistry Letters, pp. 21-24, (1991).
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
Fulton et al., *Thin fluoropolymer films and nanoparticle coatings from the rapid expansion of supercritical carbon dioxide solutions with electrostatic collection*, Polymer, vol. 44, No. 13, Jun. 2003, pp. 3627-3632.
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, European Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).
Shigeno, *Prevention of Cerebrovascular Spasm by Bosentan, Novel Endothelin Receptor*, Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 1998).
U.S. Appl. No. 11/187,467, filed Mar. 31, 2004, DesNoyer et al.
International Search Report for PCT/US2005/017690 filed May 18, 2005, mailed Dec. 1, 2005, 7 pgs.
International Search Rep. For PCT/US2007/015902, filed Jul. 12, 2007, mailed Nov. 30, 2007, 3 pgs.
Fitzgerald et al. "Investigation of the mechanisms governing the release of levamisole from poly-lactide-co-glycolide delivery systems", Journal of Controlled Release 42: pp. 125-132 (1996).
Middleton et al., "Synthetic biodegradable polymers as orthopedic devices", Biomaterials, vol. 21, pp. 2335-2346 (2000).
Roesler et al. Tris-3-(1-aziridino) propionates and their use in formulated products, Prog. Organic Coatings 50(1), pp. 1-27 (2004).
Saotome, et al., "Novel Enzymatically Degradable Polymers Comprising α-Amino Acid, 1,2-Ethanediol, and Adipic Acid", Chemistry Letters, pp. 21-24 (1991).
SIGMA-ALDRICH product information for Paclitaxel, 3pgs (2009).
Hidalgo et al., the rapamycin-sensitive signal transduction pathway as a target for cancer therapy. *Oncogene* (2000) 19: 6680-6686.
Luengo et al., Structure-activity studies of rapamycin analogs: evidence that the C-7 methoxy group is part of the effector domain and position at the FKBP12-FRAP interface. *Chemistry & Biology* (1995) 2:471-481.
Scheirs, J. (edited) Modern Fluoropolymers (1997) Chapter 31 by Claude Tournut: Thermoplastic Copolymers of Vinylidene Fluoride, *John Wiley & Sons, New York*, 22 pages.
Sedrani et al., Chemical modification of rapamycin: the discovery of SDZ RAD. *Transplantation Proc.* (1998) 30:2192-2194.
The Merck Index, Thirteenth Edition (2001), Merck & Co., Inc., Methyl Acrylate, p. 1075.
Zaragoza et al., Rapamycin Induces the $G_0$ Program of Transcriptional Repression in Yeast by Interfering with the TOR Signaling Pathway. *Molecular and Cellular Biology* (1998)18: 4463-4470.

\* cited by examiner

FIG. 2C ically beneficial coatings for implantable devices containing fluorinated polymers and methods for fabricating the same

BACKGROUND OF THE INVENTION

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, there is a great need for better coatings for the effective management of restenosis. Embodiments of the present invention disclose stent coatings having improved properties, both physical and biological.

SUMMARY

A medical article is provided, the article comprising a coating disposed on at least a portion of an implantable medical device, the coating comprising a fluorinated polymer, and a biologically beneficial polymer. Fluorinated polymers that can be used include products of polymerization of fluorinated olefins or mixtures thereof, products of polymerization of fluorinated cyclic esters, fluorine-containing cyclic polymers having a main chain with an asymmetrical cyclic structure, and copolymers of perfluoro-2,2-dimethyl-1,3-dioxole with perfluoroolefins or with perfluoro(alkyl vinyl)ethers. One example of a fluorinated polymer that can be used is poly (vinylidene fluoride-co-hexafluoropropene) available under the trade name SOLEF. Examples of biologically beneficial polymers that can be used include poly(ethylene-glycol), poly(ethylene-glycol)-block-poly(butyleneterephthalate)-block-poly(ethylene-glycol) (available under the trade name POLYACTIVE), poly(butyleneterephthalate)-block-poly (ethylene-glycol)-block poly(butyleneterephthalate), hyaluronic acid or derivatives thereof, phosphoryl choline, polyaspirin, and poly(ester amides). Biologically beneficial polymers can be optionally modified using biologically active agents such as peptides, antisense agents, rapamycin and structural derivatives or functional analogs thereof, and molecules that are sources of nitrogen oxide.

A method for fabricating a medical article is provided, the method comprises depositing a fluorinated polymer on at least a portion of an implantable medical device to form a first polymeric layer, and depositing a biologically beneficial polymer on at least a portion of the first polymeric layer to form a second polymeric layer.

DETAILED DESCRIPTION

1. Terms and Definitions

The following terms apply:

The term "biologically beneficial" refers to a product that brings about biological benefits to a patient including both therapeutic and preventative effects.

The terms "biologically degradable" or "biodegradable" refer to coatings and/or polymers that are capable of being degraded, dissolved, and/or eroded when exposed to bodily fluids such as blood and are gradually resorbed, absorbed and/or eliminated by the body. The processes of breaking down and eventual absorption and elimination of the coating and/or polymer can be caused, for example, by hydrolysis, metabolic processes, bulk or surface erosion, and the like. It is understood that after the process of degradation, dissolution, and/or erosion, has been completed, a very small to zero amount of coating or polymer will remain on the stent. Whenever the terms "degradable," "biodegradable," or "biologically degradable" are used in this application, they are intended to broadly include biologically degradable, biologically erodable, bioabsorbable, and bioresorbable coatings and/or polymers.

The term "block copolymer" is defined in accordance with the terminology used by the International Union of Pure and Applied Chemistry (IUPAC). According to the IUPAC, "block copolymer" refers to a copolymer containing a linear arrangement of blocks. The block is defined as a portion of a polymer molecule in which the monomeric units have at least one constitutional or configurational feature absent from the adjacent portions.

The term "fluorinated polymer" is defined as a polymer having at least one atom of fluorine in at least one constituent unit of the polymer.

The term "highly fluorinated polymer" is defined as any homopolymer, copolymer, terpolymer or a blend thereof in which at least 50% of monovalent atoms in the macromolecule are fluorine atoms.

The term "polymers based on fluorinated olefins" refers to the polymers which include units derived from fully or partially fluorinated olefins, such as fluorinated ethylene.

The term "non-fouling" is defined as ability of a chemical compound, such as a polymer, to delay, prevent or at least reduce a build-up of a denatured layer of protein on the stent surface or on the stent coating.

The term "conjugated" is defined as "linked," for example, covalently linked. The term "conjugating" is defined as a process of forming a link, for example, a covalent link.

The term "polymer-analogous transformation" is defined as a synthetic process of replacing functional groups in a macromolecule of the original polymer with other functional groups thus making a new polymer having new properties. The new polymer, however, retains many features of the original polymer, such as the original degree of polymerization and the structure of the backbone of the original polymer (including linear or branched nature) after the process of polymer-analogous transformation is completed.

The term "poly(ester amide)" is defined as a polymer having at least one ester fragment (I) and at least one amide fragment (II):

2. Embodiments of the Invention

A coating for an implantable medical device, such as a stent, according to embodiments of the present invention, can be a multi-layer structure that can include at least one of the following layers:
  (a) a drug-polymer layer (also referred to as "reservoir" or "reservoir layer") or alternatively a polymer free drug layer;
  (b) a primer layer;
  (c) a topcoat layer; and/or
  (d) a finishing coat layer.

Each layer of the stent coating can be formed on the stent by dissolving a polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature. For example, the coating can be baked, at a temperature such as 55° C. to 80° C.

To incorporate a drug into the reservoir layer, the drug in a form of a solution can be combined with the polymer solution that is applied onto the stent. Alternatively, to fabricate a polymer free drug layer, the drug can be dissolved in a suitable solvent or mixture of solvents, and the resulting drug solution can be applied on the stent by spraying or immersing the stent in the drug solution.

Instead of introducing the drug in a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the suitable solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The drug-polymer layer can be applied directly onto at least a part of the stent surface to serve as a reservoir for at least one active agent or a drug which is incorporated into the reservoir layer. The optional primer layer can be applied between the stent and the reservoir to improve the adhesion of the drug-polymer layer to the stent. The topcoat layer can be applied over at least a portion of the reservoir layer and serves as a rate limiting membrane which helps to control the rate of release of the drug. The topcoat layer can be essentially free from any active agents or drugs. The optional finishing coat layer can be applied over at least a portion of the topcoat layer to form the outermost layer of the stent coating to further control the rate of release of the drug. If the finishing coat layer is not used, the topcoat layer is the outermost layer of the stent coating.

The outermost layer of the stent coating can serve to provide the stent coating with biologically beneficial and/or non-fouling properties. To form the outermost layer having biologically beneficial and/or non-fouling properties, a biologically beneficial polymer can be included in the outermost layer, as discussed below in more detail. Optionally, any or all of the remaining layers of the stent coating can also include a biologically beneficial polymer. In some embodiments of the invention, additional biological benefits can be imparted to the outermost layer of the stent coating. To provide the additional biological benefits, at least one biologically active agent can be incorporated into the outermost layer of the stent coating, for example, by conjugating the biologically active agent to the biologically beneficial polymer that is present in the outermost layer.

To illustrate in more detail, in the stent coating having all four layers described above (i.e., the primer, the reservoir layer, the topcoat layer, and the finishing coat layer), the outermost layer is the finishing coat layer, which can include a biologically beneficial polymer and, optionally, an additional biologically active agent conjugated to the biologically beneficial polymer. In this case, optionally, the remaining layers (i.e., the primer, the reservoir and the topcoat layers) can also include a biologically beneficial polymer, which can be the same or different in each of the four layers.

If the finishing coat layer is not used, the stent coating can have, for example, only three layers (i.e., the optional primer, the reservoir, and the topcoat layers). The topcoat layer in this case is the outermost layer of the stent coating, which can include a biologically beneficial polymer and, optionally, an additional biologically active agent conjugated to the biologically beneficial polymer. Optionally, the primer and/or the reservoir layers can also include a biologically beneficial polymer, which can be the same or different in each of the three layers.

The polymers that can be included in the reservoir, topcoat, and/or the finishing coat layers of the stent coating are as follows.

A. The Fluorinated Layer of the Stent Coating

The stent coating, for example, the reservoir layer, can include a fluorinated polymer, for example a highly fluorinated polymer defined above. One example of a highly fluorinated polymer that can be used includes poly(vinylidene fluoride-co-hexafluoropropene) (PVDF-HFP) having a general formula (III):

Various brands of PVDF-HFP known as SOLEF family of products, available from Solvay Fluoropolymers, Inc. of Houston, Tex., can be used, for example, SOLEF 21508 having about 85 mass % of vinylidene fluoride-derived units and about 15 mass % of hexafluoro propene-derived units. PVDF-HFP is also available from Atofina Chemicals of Philadelphia, Pa., under the trade name KYNAR.

Other highly fluorinated polymers that can be used include polymers based on fluorinated olefins or mixtures thereof. Examples of some polymers belonging to this group are provided in Table 1.

TABLE 1

Examples of Olefin-Based Fluorinated Polymers Suitable for Stent Coatings.

| No. | Fluorinated Polymer | Abbreviation | General Formula |
|---|---|---|---|
| 1 | Poly(tetrafluoroethylene)*⁾ | PTFE | $-[CF_2-CF_2]_m-$ |
| 2 | Fluorinated poly(ethylene-co-propylene) | FPEP | $-[CF_2-CHF]_m-[CH_2-CH]_n-$ with $CF_3$ branch **⁾ |
| 3 | Poly(hexafluoropropene) | PHFP | $-[CF_2-CF]_n-$ with $CF_3$ branch |
| 4 | Poly(chlorotrifluoroethylene) | PCTFE | $-[CClF-CF_2]_m-$ |
| 5 | Poly(vinylidene fluoride)***⁾ | PVDF | $-[CF_2-CH_2]_m-$ |
| 6 | Poly(vinylidene fluoride-co-tetrafluoroethylene) | PVDF-TFE | $-[CF_2-CH_2]_m-[CF_2-CF_2]_n-$ |
| 7 | Poly(vinylidene fluoride-co-hexafluoropropene) | PVDF-HFP | $-[CF_2-CH_2]_m-[CF_2-CF]_n-$ with $CF_3$ branch |
| 8 | Poly(tetrafluoroethylene-co-hexafluoropropene) | PTFE-HFP | $-[CF_2-CF_2]_m-[CF_2-CF]_n-$ with $CF_3$ branch |
| 9 | Poly(tetrafluoroethylene-co-vinyl alcohol) | PTFE-VAL | $-[CF_2-CF_2]_m-[CH_2-CH]_n-$ with $OH$ branch |
| 10 | Poly(tetrafluoroethylene-co-vinyl acetate) | PTFE-VAC | $-[CF_2-CF_2]_m-[CH_2-CH]_n-$ with $OC(O)CH_3$ branch |
| 11 | Poly(tetrafluoroethylene-co-propene) | PTFEP | $-[CF_2-CF_2]_m-[CH_2-CH]_n-$ with $CH_3$ branch |
| 12 | Poly(hexafluoropropene-co-vinyl alcohol) | PHFP-VAL | $-[CF_2-CF_2]_n-[CH_2-CH]_n-$ with $CF_3$ and $OH$ branches |
| 13 | Poly(ethylene-co-tetrafluoroethylene) | PETFE | $-[CH_2-CH_2]_m-[CF_2-CF_2]_n-$ |

TABLE 1-continued

Examples of Olefin-Based Fluorinated Polymers Suitable for Stent Coatings.

| No. | Fluorinated Polymer | Abbreviation | General Formula |
|---|---|---|---|
| 14 | Poly(ethylene-co-hexafluoropropene) | PEHFP | —[CH$_2$—CH$_2$]$_m$—[CF$_2$—CF$_2$]$_n$—<br>                                                                                                                                   CF$_3$ |
| 15 | Poly(vinylidene fluoride-co-chlorotrifluoroethylene) | PVDF-CTFE | —[CF$_2$—CH$_2$]$_m$—[CClF—CF$_2$]$_m$— |

*)Including various brands of TEFLON available from E.I. DuPont de Nemours & Co. of Wilmington, Delaware.
**)The formula shows an example of one possible FPEP. Other kinds of FPEP can be used.
***)Including various brands of KYNAR.

Other highly fluorinated polymers that can be used also include polymers having heterocyclic fragments or having oxygen atoms in the backbone. These classes of polymers are not based on fluorinated olefins. Examples of such polymers include:

(1) amorphous products of polymerization of fluorinated cyclic esters, such as poly(perhalo-2,2-di-loweralkyl-1,3-dioxole-co-perfluoro-2-methylene-methyl-1,3-dioxolane) (designated for the purposes of this invention as "polyfluorooxalanes"), for example, poly(perhalo-2,2-dimethyl-1,3-dioxole-co-perfluoro-2-methylene-methyl-1,3-dioxolane);

(2) thermoplastic resinous fluorine-containing cyclic polymers having a main chain with an asymmetrical cyclic structure, with repeating units of cyclically polymerized perfluorallyl vinyl ether and/or perfluorobutenyl vinyl ether, e.g., poly(perfluorobutenyl vinyl ether) (PPBVE); and (3) copolymers of perfluoro-2,2-dimethyl-1,3-dioxole (PDD) with such monomers as perfluoroolefins and perfluoro (alkyl vinyl)ethers (designated for the purposes of this invention as "polyfluorooxoles"), including the TEFLON AF product. TEFLON AF is a trade name of a product which includes poly(tetrafluoroethylene-co-perfluoro-2,2-dimethyl-1,3-dioxole) and which is available from E.I. DuPont de Nemours & Co.

Polyfluorooxoles can contain between about 1 and 99.5% (molar) units derived from PDD and the balance of units derived from perfluoro(butenyl vinyl ether), and can optionally contain minor amounts of additional monomers, such as chlorinated or fluorinated olefins, e.g., tetrafluoroethylene or chlorotrifluoroethylene, and perfluorvinyl ethers such as perfluoropropylvinyl ether, perfluoro-3,6-dioxa-4-methyl-7-octenesulfonyl fluoride and methyl perfluoro-4,7-dioxa-5-methyl-8-nonenoate. A PPVBE brand under the trade name CYTOP, available from Asahi Glass Co. of Charlotte, N.C., can be used.

In one embodiment of the invention, a fluorinated polymer that can be used does not include any of the fluorinated polymers described above.

All fluorinated polymers used in the present invention are soluble in at least one organic solvent, or a blend of various organic solvents. Suitable solvents include fluorinated solvents, for example, fluorocarbon systems having the boiling temperature of about 60° C. to about 140° C., such as FLUORINERT FC-75 and various FREONs, and other fluorinated solvents, such as FLUX REMOVER AMS and NOVEC hydrofluoroether solvents.

FLUORINERT FC-75 is a trade name of perfluoro(2-butyltetrahydrofuran), a solvent which is available from Minnesota Mining and Manufacturing Corp. of Saint Paul, Minn. FREON is a trade name of various chlorinated fluorocarbons available from E.I. DuPont de Nemours & Co.

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and a balance of methanol, with trace amounts of nitromethane. NOVEC is a trade name of a family of solvents based on hydrofuoroethers available from 3M Corp. of St. Paul, Minn.

Other solvents can be alternatively used to dissolve the above described fluorinated polymers. Representative examples include N,N-dimethylacetamide (DMAC), N,N-dimethylformamide (DMF), dimethylsulphoxide (DMSO), acetone, cyclohexanone, methyl isobutyl ketone, methyl ethyl ketone, N-methylpyrrolidone, and 1,4-dioxane.

The reservoir layer of the stent coating can contain between greater than 0 and 100 mass % of the fluorinated polymers described above, or a blend of more than 1 of such fluorinated polymers. If less than 100% of the layer is made of the fluorinated polymers, other, alternative, polymers can comprise the balance. Examples of the alternative polymers that can be used include polyacrylates, such as poly(butyl methacrylate), poly(ethyl methacrylate), and poly(ethyl methacrylate-co-butyl methacrylate), poly(vinyl pyrrolidone), poly (hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen, and hyaluronic acid or derivatives thereof), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. In one embodiment, the blend can be free from any of these aforementioned alternative polymers.

B. The Outermost Layer of the Stent Coating

As mentioned above, the outermost layer of the stent coating can include a biologically beneficial polymer. One example of a biologically beneficial polymer that can be used is poly(ethylene glycol) (PEG). PEG is a biologically beneficial polymer, reducing smooth muscle cells proliferation at the lesion site and thus capable of inhibiting restenosis.

Another example of a biologically beneficial polymer that can be used is a block-copolymer of PEG with poly(butyleneterephthalate) (PBT), such as poly(ethylene-glycol)-block-poly(butyleneterephthalate)-block-poly(ethylene-glycol) (PEG-PBT-PEG). This block-copolymer can be obtained, for example, by trans-esterification of dibutyleneterephthalate with PEG.

PEG-PBT-PEG block copolymer is known under a trade name POLYACTIVE and is available from IsoTis Corp. of Holland. In PEG-PBT-PEG, the ratio between the units derived from ethylene glycol and the units derived from butylene terephthalate can be between about 0.67:1 and about 9:1. The molecular weight of the units derived from ethylene glycol can be between about 300 and about 4,000 Daltons. Alternatively, if desired, the positions of the moieties in the PEG-PBT-PEG block copolymer can be switched to obtain a BAB block copolymer, poly(butyleneterephthalate)-block-poly(ethylene-glycol)-block poly(butyleneterephthalate) (PBT-PEG-PBT).

Both PEG-PBT-PEG and PBT-PEG-PBT block copolymers contain fragments with ester bonds. Ester bonds are known to be water-labile bonds. When in contact with slightly alkaline blood, ester bonds are subject to catalyzed hydrolysis, thus ensuring biological degradability of the block-copolymer. One product of degradation of either PEG-PBT-PEG or PBT-PEG-PBT is expected to be PEG, which is biologically beneficial as described above. As a result, including either PEG-PBT-PEG or PBT-PEG-PBT in the outermost layer of the stent coating is expected to provide the coating with biologically beneficial properties.

In addition to PEG and POLYACTIVE polymers, other biologically beneficial polymers can be included in the outermost layer of the stent coating. Examples of such alternative biologically beneficial polymers include hyaluronic acid or derivatives thereof, poly(ethylene oxide-co-propylene oxide) phosphoryl choline, polyaspirin, and polymers of the class of poly(ester amides). One brand of poly(ethylene oxide-co-propylene oxide) that can be used is available from BASF Corp. of Parsippany, N.J. under the trade name PLURONIC.

Poly(ester amides) are polymers having a general formula (IV):

$$-[M\text{-}P]_m\text{-}[M\text{-}Q]_n\text{-} \qquad (IV)$$

wherein M is a moiety represented by the structure

P can include any of the following moieties (P1)-(P4):

(P1)

(P2)

—O—X—O— ; or (P3)

—NH—Y—NH— ; and (P4)

Q can include any of the following moieties (Q1)-(Q4):

(Q1)

(Q2)

—O—Z—O— , or (Q3)

—NH—Z—NH— . (Q4)

$R_1$ can be a straight chained or branched aliphatic alkylene group $C_nH_{2n}$, and n can be an integer having the value between 2 and 12, e.g. ethylene, propylene, butylene, amylene (pentylene), hexylene, heptylene, octylene, nonylene, decylene, undecylene, or dodecylene group, or an aromatic group, e.g., para-phenylene.

$R_2$ can be hydrogen; methyl ($CH_3$); iso-propyl (i-$C_3H_7$); sec-butyl (sec-$C_4H_9$); iso-butyl (i-$C_4H_9$); or benzyl ($C_6H_5$—$CH_2$).

$R_3$ can be methylene ($CH_2$); methylmethylene ($CHCH_3$); n-propylene ($CH_2CH_2CH_2$); iso-propylene ($CH_2CHCH_3$); ethylmethylene ($CHCH_2CH_3$); straight chained or branched butylene, such as n-butylene ($CH_2CH_2CH_2CH_2$), iso-butylene [$CH_2CH(CH_3)CH_2$], and sec-butylene [$CH(CH_2CH_3)CH_2$]; or n-amylene ($CH_2CH_2CH_2CH_2CH_2$).

X can be a straight chained or branched aliphatic alkylene group $C_nH_{2n}$, and n can be an integer between 2 and 12, e.g., methylene, ethylene, propylene, butylene, amylene (pentylene), hexylene, heptylene, octylene, nonylene, decylene, undecylene, or dodecylene group.

Y can be straight chained or branched aliphatic alkylene group $C_2H_4$ (ethylene), $C_4H_8$ (butylene), or $C_5H_{10}$ (amylene or pentylene).

Z can be a biologically beneficial moiety derived from PEG, poly(propylene glycol), hyaluronic acid or derivatives thereof, poly(2-hydroxyethyl methacrylate) or cellulosics; and m and n, are integers.

One example of poly(ester amide) that can be used includes products of reaction between diol-diamines and dicarboxylic acids, one unit of which is shown by the general formula (V).

(V)

wherein R can be selected from a group consisting of hydrogen; methyl, iso-propyl, sec-butyl, iso-butyl, or benzyl; x is an integer having a value between 2 and 12; and y is an integer having a value between 1 and 12.

The outermost layer of the stent coating can contain between greater than 0 and 100 mass % of the biologically beneficial polymers described above, or a blend of more than 1 of such biologically beneficial polymers. In one embodiment of the invention, a biologically beneficial polymer that can be used does not include any of the biologically beneficial polymers described above.

If less than 100% of the layer is made of the biologically beneficial polymers, other, alternative, polymers can comprise the balance. Examples of the alternative polymers that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly(vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. In one embodiment, the stent coating can be free of any of these additional polymers.

The therapeutic substance which can be used in the reservoir layer can include any substance capable of exerting a therapeutic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

To provide more biological benefits, at least one additional biologically active agent can be optionally incorporated into the outermost layer of the stent coating, for example, by conjugating the biologically active agent to the biologically beneficial polymer that is present in the outermost layer. As a result of conjugation, an adduct of the biologically active agent and the biologically beneficial polymer can be formed. The adduct can be then used for making the outermost layer. For example, the adduct can be dissolved in a suitable solvent, or a mixture of solvents, and the resulting solution of the adduct can be applied on the stent as described above.

The additional biologically active agent can include any substance capable of exerting a therapeutic or prophylactic effect in the practice of the present invention. Some examples of drugs that can be used for conjugation with PEG or POLY- ACTIVE block-copolymer include peptides such as polyarginine (e.g., R7) or c-RGD, antisense agents (e.g., Rensten-NG), rapamycin and structural derivatives or functional analogs thereof, such as EVEROLIMUS, 40-O-(3-hydroxy) propyl-rapamycin, 40-O-[2-(2-hydroxy)ethoxy]ethyl-rapamycin, and 40-O-tetrazole-rapamycin, and molecules that are sources of nitrogen oxide (NO) such as diazenium diolates.

One method of conjugating an additional biologically active agent to PEG or POLYACTIVE block-copolymer is by reactions of polymer-analogous transformation of PEG or POLYACTIVE block-copolymer, utilizing the reactive functional groups of PEG or the copolymer. For instance, the free hydroxyls of PEG or the PEG blocks can be used for conjugating. An example of an additional biologically active agent that can be conjugated to PEG or POLYACTIVE block-copolymer is a diazenium diolate type nitric oxide donor and the process of conjugating can be carried out as described below.

Diazenium diolate type nitric oxide donors are adducts of nitric oxide with nucleophilic amines. Diazenium diolates, also known as "NONOates," are highly biologically compatible, and in slightly acidic medium they spontaneously release NO. One example of diazenium diolate that can be used is spermine diazenium diolate (SDD).

SDD, also known by its chemical name as 1,3-propanediamine, N-{4-[1-(3-aminopropyl)-2-hydroxy-2-nitrosohydrazino]butyl}-diazen-1-ium-1,2-diolate, is aliphatic NON-Oate having the formula $NH_2-(CH_2)_3-N[N^+(O)-N^--OH)]-(CH_2)_4-NH-(CH_2)_3-NH_2$. SDD is available from Molecular Probes, Inc. of Eugene, Oreg. Alternatively, other diazenium diolate-type NO donors can be used. Some examples of the alternative diazenium diolate-type NO donors that can be conjugated to the PEG blocks of PEG-PCL-PEG include 1-{N-methyl-N-[6-(N-methylammonio) hexyl]amino}diazen-1-ium-1,2-diolate having the formula $CH_3-N^+H_2-(CH_2)_6-N(CH_3)-N^+(O^-)=N-O^-$ (MAHMA-NO), and Z-1-[N-(2-aminoethyl)-N-(2-ammonioethyl)amino]diazen-1-ium-1,2-diolate having the formula $O-N^+[N(CH_2CH_2NH_2)CH_2CH_2N^+H_3]=N-O^-$ (DETA-NO). MAHMA-NO and DETA-NO can be obtained from Cayman Chemical Co. of Ann Arbor, Mich.

To conjugate SDD to PEG, PEG can be preliminarily derivatized by tosylation (treatment with tosyl chloride), or alternatively by tresylation (by reacting with tresyl chloride). Tosyl chloride is a derivative of toluene, para-toluenesulfonyl chloride having the formula $CH_3-C_6H_4-SO_2Cl$ (TsCl). The process of tosylation includes an attack on the terminal hydroxyl of the PEG molecule and can be illustrated by reaction (VI):

$$HO-[CH_2-CH_2-O]_p-H+CH_3-C_6H_4-SO_2Cl \rightarrow H-[O-CH_2CH_2]_p-O-SO_2-C_6H_4-CH_3+HCl \quad (VI)$$

Alternatively, tresyl chloride (2,2,2-trifluoroethanesulphonyl chloride) can be used to derivatrize PEG. The process of tresylation also includes an attack on the terminal hydroxyl of the PEG molecule and can be illustrated by reaction (VII:

$$HO-[CH_2-CH_2-O]_p-H+CF_3-CH_2-SO_2Cl \rightarrow H-[O-CH_2CH_2]_p-O-SO_2-CH_2-CF_3+HCl \quad (VII)$$

Next, tosylated or tresylated PEG can be modified by conjugating SDD. Due to the presence of two primary and one secondary amino groups, SDD is readily conjugated to the tosylated or tresylated PEG via alkylation of the amino groups. One possible process of conjugating can be shown for tosylated PEG as reaction (VIII):

$$H-[O-CH_2-CH_2]_p-O-SO_2-C_6H_4-CH_3 \quad (VIII)$$

Since POLYACTIVE block-copolymer includes two terminal PEG blocks (as can be seen from the formula PEG-PBT-PEG), the process similar to those described by reactions (VI-VIII) can be also used to modify POLYACTIVE block-copolymer by conjugating SDD to one or both PEG blocks that are present in the POLYACTIVE block-copolymer. SDD can be also conjugated to PBT-PEG-PBT block-copolymer, using terminal carboxyl groups of that are present in the PBT blocks of PBT-PEG-PBT copolymer. One or both PBT blocks of PBT-PEG-PBT block-copolymer can be used for conjugating SDD. Those having ordinary skill in the art can determine under which conditions the two-step process of conjugating SDD to PEG, POLYACTIVE, or PBT-PEG-PBT block-copolymer described above can be carried out.

The resulting polymeric adducts can be described schematically as:
(a) Dz-PEG-PBT-PEG (one PEG block of POLYACTIVE is modified);
(b) Dz-PEG-PBT-PEG-Dz (two PEG blocks of POLYACTIVE are modified);
(c) PEG-Dz (PEG is modified);
(d) Dz-PBT-PEG-PBT (one PBT block of PBT-PEG-PBT copolymer is modified); and
(e) Dz-PBT-PEG-PB-Dz (two PBT blocks of PBT-PEG-PBT copolymer are modified), where Dz is a fragment derived from SDD.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

3. Examples

The following examples are provided to further illustrate embodiments of the present invention.

Example 1

A first composition was prepared by mixing the following components:
(a) about 2.0 mass % poly(butyl methacrylate) (PBMA); and
(b) the balance, a solvent blend comprising acetone and cyclohexanone in a mass ratio of about 7:3.

The first composition was applied onto the surface of a bare 18 mm VISION stent (available from Guidant Corporation) by spraying and dried to form a primer layer. A spray coater was used having a 0.014 fan nozzle maintained at about 60° C. with a feed pressure of about 0.2 atm (about 3 psi) and an atomization pressure of about 1.3 atm (about 20 psi). The primer was dried and baked at about 50° C. for about 1 hour, yielding a dry primer layer containing about 80 µg of PBMA.

A second composition was prepared by mixing the following components:
(a) about 2.0 mass % SOLEF 21508;
(b) about 1.0 mass % EVEROLIMUS; and
(c) the balance, a solvent blend comprising acetone and cyclohexanone in a mass ratio of about 7:3.

The second composition contained about 300 µg SOLEF and about 200 µg EVEROLIMUS. The second composition was applied onto the dried primer layer to form the reservoir layer, using the same spraying technique and equipment used for applying the primer layer, followed by drying and baking at about 50° C. for about 2 hours.

A third composition was prepared by mixing the following components:
(a) about 2.0 mass % POLYACTIVE containing about 45 molar % PBT units and about 55 molar % PEG units; the molecular weight of the PEG units was about 300 Daltons;
(b) the balance, a solvent blend, the blend comprising 1,1,2-tricloroethane and chloroform in a mass ratio of about 4:1.

The third composition was applied onto the dried reservoir layer to form a topcoat layer, using the same spraying technique and equipment used for applying the primer layer and the reservoir layer, followed by drying and baking at about 50° C. for about 2 hours, yielding a dry topcoat layer containing about 250 µg of POLYACTIVE.

The coated stent was subjected to simulated testing according to the following procedure. The stent was installed on a catheter and guided through a tortuous path and then deployed in a poly(vinyl alcohol) lesion having approximate size of about 3 by 10 millimeters. The tortuous path and the lesion contained de-ionized water at about 37° C. To deploy the stent, pressure of about 16 atm was applied to the balloon for about 1 minute, followed by deflating of the balloon and retraction of the catheter. After the catheter was retracted, de-ionized water was pumped through the tortuous path and the lesion for about 1 hour at a rate of about 50 milliliters per minute. Water was maintained at about 37° C.

Figure 1A:
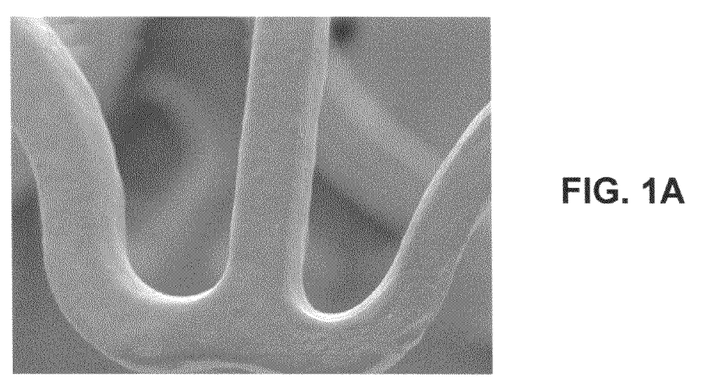
FIGS. 1A, 1B, and 1C show the microphotographs demonstrating overall views of the outer surface of the stent coated according to an embodiment of the present invention after the simulated in vitro testing.
Figure 1B:
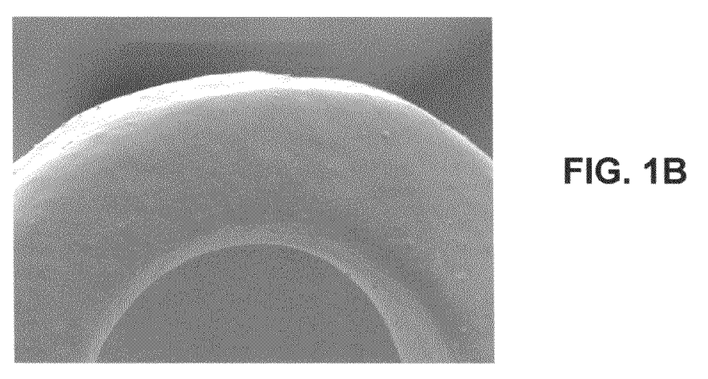
Figure 1C:
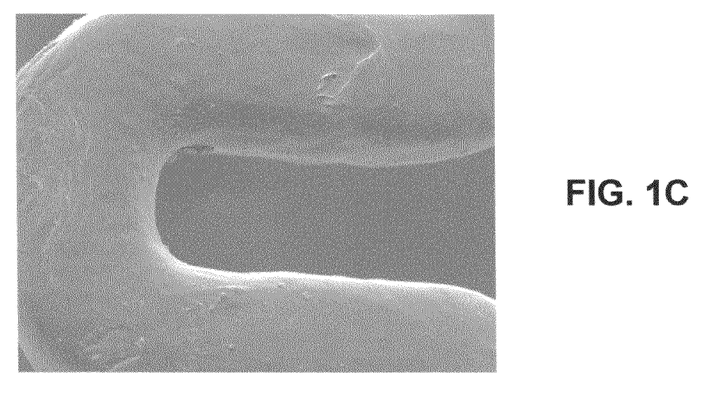
Figure 2A:
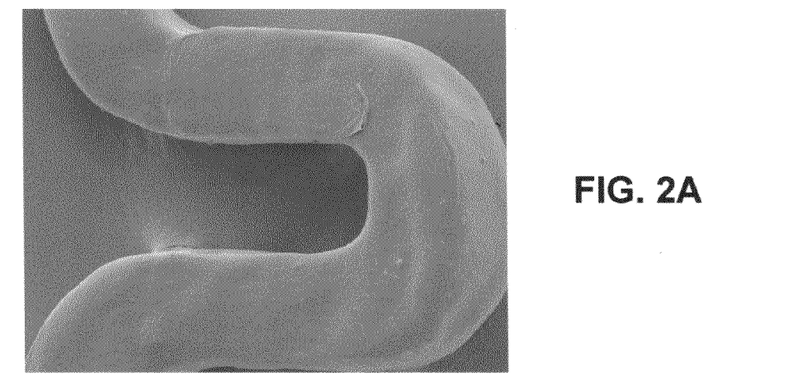
FIGS. 2A, 2B, and 2C show the microphotographs demonstrating overall views of the inner surface of the stent coated according to an embodiment of the present invention after the simulated in vitro testing.
Figure 2B:
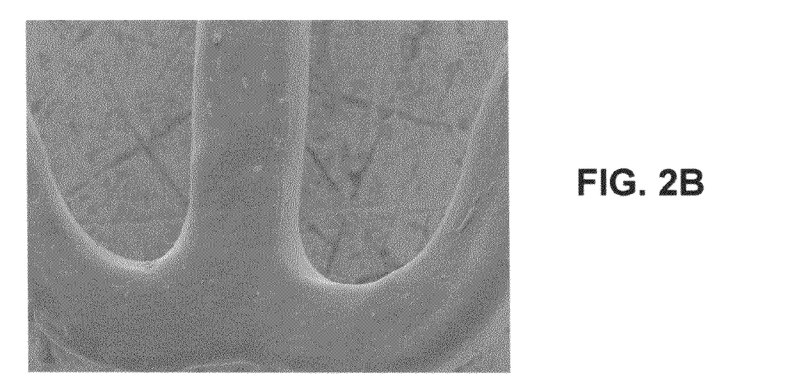
Figure 2C:
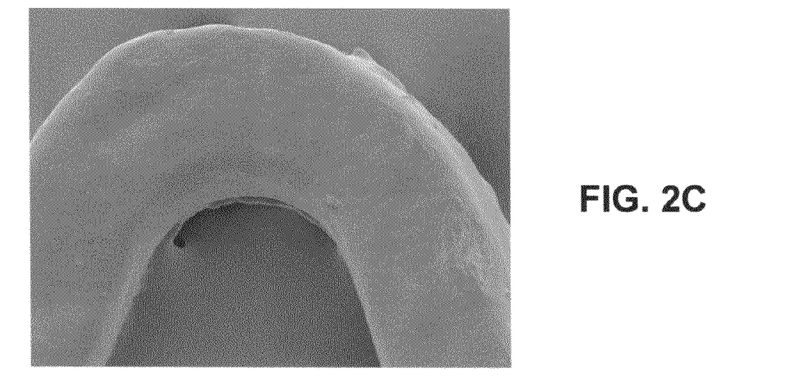

Overall views of the coated stent which underwent the simulated in-vitro testing are shown by the microphotographs on FIGS. 1A, 1B, 1C, 2A, 2B and 2C. After the simulated use test, the quality of the stents coatings was good. No damage of the coatings on the outer surface area (FIGS. 1A, 1B, and 1C) or inner surface area (FIGS. 2A, 2B, and 2C) was observed.

Example 2

The primer layer can be formed on an 18 mm VISION stent as described in Example 1.

A first composition can be prepared by mixing the following components:
(a) between about 0.5 mass % and about 2.5 mass %, for example, about 2.0 mass % EVEROLIMUS; and
(b) the balance, a solvent blend comprising acetone and xylene in a mass ratio of about 2:3.

The first composition can contain about 300 µg EVEROLIMUS. The composition can be applied onto the dried primer layer to form the reservoir layer, using the same spraying technique and equipment used for applying the primer layer, followed by drying and baking at about 50° C. for about 1 hour.

A second composition can be prepared by mixing the following components:
(a) between about 1.0 mass % and about 15 mass %, for example, about 2.0 mass % SOLEF 21508; and
(b) the balance, a solvent blend comprising acetone and cyclohexanone in a mass ratio of about 7:3.

The second composition can be applied onto the dried reservoir layer to form the topcoat layer, using the same spraying technique and equipment used for applying the primer layer, followed by drying and baking at about 50° C. for about 2 hours, yielding a dry topcoat layer containing about 300 µg of SOLEF.

A third composition can be prepared by mixing the following components:
(a) between about 1.0 mass % and about 15 mass %, for example, about 2.0 mass % poly(ester amide); and
(b) the balance, ethanol.

The third composition can be applied over the dried topcoat layer using techniques described above, followed by drying and baking at about 50° C. for about 2 hours, yielding a dry finishing coat layer containing about 150 µg of poly(ester amide).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A medical article comprising a coating disposed on at least a portion of an implantable medical device, the coating comprising:
(a) a fluorinated polymer; and
(b) a biologically beneficial polymer;
wherein the fluorinated polymer is selected from the group consisting of:
(i) products of polymerization of fluorinated olefins;
(ii) fluorine-containing cyclic polymers having a main chain with an asymmetrical cyclic structure selected from a group consisting of polymers of repeating units of cyclically polymerized perfluorallyl vinyl ether, perfluorobutenyl vinyl ether, and a combination thereof; and
(iii) copolymers of perfluoro-2,2-dimethyl-1,3-dioxole with perfluoroolefins or with perfluoro(alkyl vinyl) ethers;

wherein the biologically beneficial polymer is selected from the group consisting of poly(ester amide) polymers of a general formula

-[M-P]$_m$-[M-Q]$_n$-, and combinations of these poly(ester amide) polymers, wherein M is a moiety represented by the structure P is a moiety selected from a group (P1)-(P4) consisting of:

(P1)

(P2)

, and (P3)

; (P4)

Q is a moiety selected from a group (Q1)-(Q4) consisting of:

(Q1)

(Q2)

, and (Q3)

; (Q4)

wherein:
R$_1$ is selected from a group consisting of a straight chained or branched aliphatic alkylene group C$_r$H$_{2r}$, wherein r is an integer having the value between 2 and 12, and an aromatic group;
R$_2$ is selected from a group consisting of hydrogen, methyl, iso-propyl, sec-butyl, iso-butyl, and benzyl;
R$_3$ is selected from a group consisting of methylene, methylmethylene, n-propylene, iso-propylene, ethylmethylene, straight chained or branched butylene, and n-amylene;
X is a straight chained or branched aliphatic alkylene group C$_x$H$_{2x}$, wherein x is an integer between 2 and 12;
Y is a straight chained or branched aliphatic alkylene group C$_y$H$_{2y}$, wherein y is 2, 4, or 5;

Z is a biologically beneficial moiety derived from poly(ethylene glycol), poly(propylene glycol), hyaluronic acid, poly(2-hydroxyethyl methacrylate);
and
m and n are integers;
and
wherein the biologically beneficial polymer is conjugated to a biologically active agent.

2. The medical article of claim 1, wherein the implantable medical device is a stent.

3. The medical article of claim 1, wherein the fluorinated polymer is selected from the group consisting of products of polymerization of fluorinated olefins, and combinations of these polymers.

4. The medical article of claim 1, wherein the fluorinated polymer is selected from the group consisting of copolymers of perfluoro-2,2-dimethyl-1,3-dioxole with perfluoroolefins or with perfluoro(alkyl vinyl)ethers, and combinations of these polymers.

5. The medical article of claim 1, wherein the fluorinated polymer is selected from the group consisting of polymers of repeating units of cyclically polymerized perfluorallyl vinyl ether, perfluorobutenyl vinyl ether, and combinations of these polymers.

6. The medical article of claim 1, wherein the biologically active agent is selected from the group consisting of polyarginine, cRGD peptide, antisense agent Rensten-NG, rapamycin, everolimus (40-O-(2-hydroxy)ethyl-rapamycin), 40-O-(3-hydroxy)propyl-rapamycin, 40-O-[2-(2-hydroxy)ethoxy]ethyl-rapamycin, 40-O-tetrazole-rapamycin, diazenium diolates, and combinations thereof.

7. The medical article of claim 6, wherein the diazenium diolates are selected from the group consisting of 1,3-propanediamine, N-{4-[1-(3-aminopropyl)-2-hydroxy-2-nitrosohydrazino]butyl}-diazen-1-ium-1,2-diolate (SDD), 1-{N-methyl-N-[6-(N-methylammonio)hexyl]amino}diazen-1-ium-1,2-diolate (MAHMA-NO), Z-1-[N-(2-aminoethyl)-N-(2-ammonioethyl)amino]diazen-1-ium-1,2-diolate (DETA-NO), and combinations thereof.

8. The medical article of claim 1, wherein the coating comprises two or more layers, the fluorinated polymer and the biobeneficial polymer being in separate layers, and the outermost layer comprising the biobeneficial polymer.

9. The medical article of claim 1, wherein the biologically active agent is selected from the group consisting of rapamycin, everolimus (40-O-(2-hydroxy)ethyl-rapamycin), 40-O-(3-hydroxy)propyl-rapamycin, 40-O-[2-(2-hydroxy)ethoxy]ethyl-rapamycin, 40-O-tetrazole-rapamycin, and combinations thereof.

10. The medical article of claim 9, wherein the outermost layer of the coating covers the entire surface area of the implantable device.

11. The medical article of claim 1, wherein the Z of the poly(ester amide) polymers is poly(ethylene glycol).

12. The medical article of claim 1, wherein the Z of the poly(ester amide) polymers is poly(propylene glycol).

13. The medical article of claim 1, wherein the Z of the poly(ester amide) polymers is hyaluronic acid.

14. The medical article of claim 1, wherein the Z of the poly(ester amide) polymers is poly(2-hydroxyethyl methacrylate).

* * * * *